United States Patent [19]

Lapidus

[11] 4,124,578
[45] Nov. 7, 1978

[54] ANTIOVULATORY POLYPEPTIDES

[75] Inventor: Milton Lapidus, Rosemont, Pa.

[73] Assignee: American Home Products Corporation, New York, N.Y.

[21] Appl. No.: 866,727

[22] Filed: Jan. 3, 1978

[51] Int. Cl.$^2$ .................... C07C 103/52; A61K 37/00
[52] U.S. Cl. .......................... 260/112.5 LH; 424/177
[58] Field of Search ............... 260/112.5 LH; 424/177

[56] References Cited
PUBLICATIONS

Change, et al., Biochem. & Biophys. Res. Comm., 44, 409(1971) & 44, 414 (1971).
Chang, et al., Biochem. & Biophys. Res. Comm., 47, 1256 (1972).

*Primary Examiner*—Delbert R. Phillips

[57] ABSTRACT

Peptides of the formula:

pGlu-Tyr-Arg-X-Y wherein:
 X is Trp or D-Trp, and
 Y is Pro-NHEt or the peptide segment —Gly—X$_1$—X$_2$—Arg—Pro—Z, wherein:
  X$_1$ is Ala, D-Ala, or MeAla;
  X$_2$ is Leu or D-Leu; and
  Z is —NH$_2$ or —NHEt,
or the non-toxic pharmaceutically acceptable acid addition salts thereof, inhibit ovulation in warm-blooded animals.

5 Claims, No Drawings

ANTIOVULATORY POLYPEPTIDES

The synethetic tetrapeptide pGlu—Tyr—Arg—Trp—NH$_2$ has been reported to release luteinizing hormone (LH) in vivo in the rat. Follicle stimulating hormone (FSH) release is, however, unaffected. [Chang et al., *Biochem. and Biophys. Res. Comm.*, 44, 409 (1971) and Bowers, *Biochem. and Biophys. Res. Comm.*, 44, 414 (1971)]. The heptapeptide pGlu—Tyr—Arg—Trp—Gly—His—Leu—NH$_2$, which is a chain extension of the aforesaid tetrapeptide, has been found also to release LH in the rat [Chang, *Biochem. and Biophys. Res. Comm.*, 47, 1256 (1972)]. Both peptides contain amino acid residues in common with the luteinizing hormone-release hormone (LH-RH) which has the amino acid sequence:

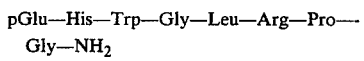

pGlu—His—Trp—Gly—Leu—Arg—Pro—Gly—NH$_2$

However, the sequence of amino acid residues in the peptides of Chang et al. is entirely different from the sequence of LH—RH.

The present invention comprises synthetic peptides of the formula:

pGlu—Tyr—Arg—X—Y      I wherein:
X is Trp or D-Trp, and
Y is Pro—NHEt or the peptide segment —Gly—X$_1$—X$_2$—Arg—Pro—Z, wherein:
X$_1$ is Ala, D-Ala, or MeAla;
X$_2$ is Leu or D-Leu, and
Z is —NH$_2$ or —NHEt, or a non-toxic pharmaceutically acceptable addition salt thereof.

All optically active amino acids or optically active amino acid residues in the peptides described herein are in the natural or L-configuration, unless otherwise indicated. The abbreviations used for the amino acids and amino acid residues are standard in the art. "pGlu" means pyroglutamic acid (5-oxoproline) and "MeAla" means α-methyl alanine. The symbol "Et" means the ethyl group.

The compounds of this invention, i.e. the compounds of Formula I wherein X and Y have the meanings herein-above defined, have pharmacological activity. Specifically, they inhibit spontaneous ovulation in female warm-blooded animals, as evidenced by standard pharmacological testing in the rat. The compounds of Formula I are therefore useful as anti-fertility agents when administered to female warm-blooded animals.

The compounds described herein may be administered to female warm-blooded animals either intravenously, subcutaneously, intramuscularly, or orally to inhibit ovulation. The active ingredient may be administered alone or in combination with pharmaceutically acceptable carriers or excipients. Suitable pharmaceutical compositions will be apparent to those skilled in the art.

Preferred peptides of Formula I are those wherein:
a. X is D-Trp; Y is —Gly—(MeAla)—D—Leu—Arg—ProNHEt,
b. X is Trp; Y is —Gly—D—Ala—Leu—Arg—ProNHEt.
c. X is Trp; Y is —Gly—D—Ala—Leu—Arg—Pro—NH$_2$.
d. X is Trp; Y is —ProNHEt.

The preparation of the preferred embodiments, described above, is described in the Examples. The preparation of other embodiments can be carried out using the methods and procedures set forth in the Examples, or obvious modifications thereof. A desired embodiment can be prepared using the described techniques by substituting an appropriate amino acid or protected amino acid for a particular amino acid or protected amino acid illustrated in the Examples.

The polypeptides of this invention are prepared by solid phase methodology, following techniques generally known in the art for building an amino acid sequence from an initial resin supported amino acid. Merrifield, *J.A.C.S.*, 85, 2149 (1963) generally illustrates the technique involved.

As applied to the compounds of this invention, α-amino protected proline is attached to a chloromethylated polystyrene resin or a benzhydryl amine polystyrene resin and the α-amino protecting group is removed with trifluoroacetic acid in methylene chloride. The deprotection is conducted at a temperature between about 0° C. and room temperature. Other standard cleaving reagents and conditions for removal of specific α-amino protecting groups may be used as described in Schroder E. Lubke, "The Peptides", 1, 72-75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., *Analyt. Biochem.*, 34, 595 (1970). Where incomplete coupling has occurred, the reaction is repeated before the α-amino protecting group is removed for introduction of the next amino acid or amino acid sequence. The preferred coupling reagent employed is diisopropylcarbodiimide, but other reagents will be apparent to those skilled in the art.

After the desired amino acid sequence has been synthesized, the polypeptide is removed from the resin support by conventional methods. When a chloromethylated polystyrene resin is used, the cleavage is accomplished by treatment with ethyl amine which forms the ethylamide of the terminal amino acid residue. When a benzhydryl amine resin is used, treatment with hydrogen fluoride-anisole cleaves the polypeptide from the resin and directly forms the amide of the terminal amino acid residue. The side chain protecting groups are then removed conventionally by treatment with hydrogen fluoride.

Non-toxic pharmaceutically acceptable acid addition salts of the polypeptides are produced by methods well known in the art from hydrochloric, hydrobromic, sulfuric, phosphoric, polyphosphoric, maleic, acetic, citric, benzoic, succinic, malonic, or ascorbic acid and the like.

The protecting groups employed throughout the solid phase synthesis are well known to the art. In selecting a particular side chain protecting group to be used in the synthesis of the peptides of this invention, the following rules should be followed: (a) the side chain protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

Preferred protecting groups are tert-butyloxycarbonyl (t-Boc), for protecting and α-amino group; benzyl (Bzl), for protecting a side chain hydroxy group; and tosyl, for protecting a side chain guanadine.

The following Examples illustrate and demonstrate the processes of making and using the compounds of the invention:

EXAMPLE 1

L-(5-oxoprolyl)-O-benzyl-L-tyrosyl-N$^g$-tosyl-L-arginyl-D-tryptophylglycyl-(2-methylalanyl)-D-leucyl-N$^g$-tosyl-L-arginyl-L-prolylpolystyrene resin ester

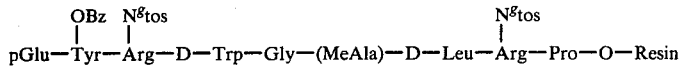

A mixture of tert-butyloxycarbonylproline (t-Boc-proline) (10.3 g., 0.048 mole), potassium t-butoxide (4.9 g., 0.44 mole), and polystyrene resin (Bio-Rad SX-1, 200–400 mesh) (24 g., 18 meq. Cl) in 100 ml dimethylsulfoxide are stirred in a 1 liter reaction vessel at 80° C for four hours. Stirring is continued overnight at room temperature. The t-Boc-proline resin is collected on a sintered glass funnel and washed as follows with a 200 ml. portion of each solvent: ethanol (three times), methanol (three times), methylene chloride (three times), methanol (two times), and methylene chloride (three times). The t-Boc-proline resin is dried overnight in a vacuum oven at room temperature. Amino acid analysis indicates substitution on the resin of 0.63 mmoles of amino acid per g. or resin.

The t-Boc-proline resin (6 g., 3.78 mmole) is placed in a 200 ml. reaction vessel and treated as follows:
1. Wash with methylene chloride (three times).
2. Pretreat with 38% (v/v) trifluoroacetic acidmethylene chloride containing 0.5% dithioerythritol for 5 minutes.
3. Treat for 25 minutes using the reagent employed in step 2.
4. Wash with methylene chloride (three times).
5. Wash with dimethylformamide (DMF) (three times).
6. Pretreat with 15% trethylamine —DMF for 1 minute.
7. Treat for 10 minutes using reagent employed in step 6.
8. Wash with DMF (three times).
9. Wash with methylene chloride (three times).

A contact time for two minutes is allowed for each step unless otherwise stated. The deprotected amino acid resin gives a positive ninhydrin test according to the procedure of E. Kaiser et al., Anal. Chem., 34, 595 (1970).

10. The proline-resin is gently stirred overnight with t-Boc-N$^g$-tosyl-L-arginine (6420 mg., 15 mmoles) and N,N-diisopropylcarbodiimide (18 mmoles) in 1:1 DMF-methylene chloride. The peptide-resin is then treated as follows:
11. Wash with DMF (three times).
12. Wash with methanol (three times).
13. Wash with methylene chloride (three times).

The peptide-resin gives a negative ninhydrin test. The t-Boc-α-amino protecting group is removed as described in steps (1) through (9) above.

The following amino acid residues are then introduced consecutively:
t-Boc-D-leucine (3469 mg., 15 mmoles);
t-Boc-α-methylalanine (3048 mg., 15 mmoles);
t-Boc-glycine (2625 mg., 15 mmoles);
t-Boc-D-tryptophane (4560 mg., 15 mmoles);
t-Boc-N$^g$-tosyl-L-argine (6420 mg., 15 mmoles);
t-Boc-O-benzyl-L-tyrosine (5565 mg., 15 mmoles);
and pyroglutamic acid (1935 mg., 15 mmoles).

Each coupling reaction is carried out by stirring the protected amino acid overnight with the peptide-resin and N,N-diisopropylcarbodiimide (18 mmoles) in 1:1 DMF-methylene chloride. Following each coupling reaction the peptide-resin is treated as described in steps (11) through (13). Removal of the α-amino protecting group (t-Boc) after each coupling reaction is performed as described in steps (1) through (9). After the final washing, the peptide-resin is dried in vacuo.

EXAMPLE 2

L-(5-oxoproyl)-O-benzyl-L-tyrosyl-N$^g$-tosyl-L-arginyl-D-tryptophylglycyl-(2-methylalanyl)-D-leucyl-N$^g$-tosyl-L-arginyl-N-ethyl-L-prolinamide The protected peptide resin from Example 1 and ethyl amine (100 ml. are stirred overnight in a glass pressure bottle. The resin is collected and washed with dimethylformamide (three times, 50 ml.). The filtrate and washes are combined, and the solvents are removed. The residue is triturated with ether, collected, and dried in a vacuum desicator. Yield: 3.4 g.

EXAMPLE 3

L-(5-Oxoprolyl)-L-tyrosyl-L-arginyl-D-tryptophylglycyl-(2-methylalanyl)-D-leucyl-L-arginyl-N-ethyl-L-prolinamide The peptide from Example 2 (3.4 g.) is treated in vacuo with anhydrous liquid hydrogen fluoride (85 ml.). and anisole (15 ml.) at 0° C. for 1 hour. The hydrogen fluoride and anisole are removed under reduced pressure, and the residue is dissolved in 2 N acetic acid (100 ml.). Lyophilization yields 2.5 g. of the crude title peptide. A 1.0 g. sample of the crude material is purified as follows:

The sample, dissolved in 4 N acetic acid, is passed through a column (2.5 × 200 cm.) of Sephadex G-15. The effluent is monitored automatically by means of a recorder and flow cell (254 mµ.). Fractions 100–110 are combined and lyophillized to give 182 mg. of product. The product is further purified by partition chromatography by dissolving a 180 mg. sample in the upper phase of n-butanol-water-acetic acid (4:5:1) and applying the system to a column (2.5 × 200 cm.) of Sephadex G-15. The effluent is monitored as above. Fractions 60–77 are combined. Removal of the solvent and lyophillization of the residue yields 75 mg. of purified title peptide. This material is homogeneous as shown by thin layer chromatography [n-butanol-ethyl acetateacetic acid-water (1:1:1:1); visualized with chlorine peptide reagent].

EXAMPLE 4

L-(5-Oxoprolyl)-O-benzyl-L-tyrosyl-N$^g$-tosyl-L-arginyl-L-tryptophylglycyl-D-alanyl-L-leucyl-N$^g$-tosyl-L-arginyl-L-prolylpolystyrene resin ester

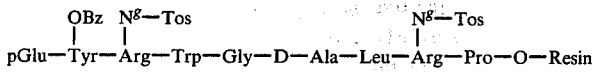

The title peptide resin is prepared and purified by the procedures described in Example 1 from 6 g. of t-Boc-L-prolyl-resin ester. In the procedure, t-Boc-L-tryptophan replaces t-Boc-D-tryptophan, T-Boc-D-alanine replaces α-methylalanine, and t-Boc-L-leucine replaces t-Boc-D-leucine.

EXAMPLE 5

L-(5-Oxoprolyl)-L-tyrosyl-L-arginyl-L-tryptophylglycyl-D-alanyl-L-leucyl-L-arginyl-N-ethyl-L-prolinamide The peptide resin from Example 4 is treated with ethylamine according to procedure described in Example 2 to cleave the blocked peptide from the resin. Yield: 4.2 g. Deblocking as with hydrogen-fluoride-anisole according to the procedure described in Example 2 yields 3.1 g. of the crude title peptide. Purification of a 1 g. sample of the crude material in the manner described in Example 3 gives 132 mg. of the title peptide, shown to be homogeneous by thin-layer chromatography.

EXAMPLE 6

L-(5-Oxoprolyl)-O-benzyl-L-tyrosyl-N$^g$-tosyl-L-arginyl-L-tryptophylglycyl-D-alanyl-L-leucyl-N$^g$-tosyl-L-arginyl-L-prolyl-polystyrene resin amide

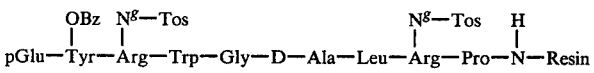

The title peptide resin is prepared by the Merrifield solid phase method starting with 5 g. of benzhydryl amine polystyrene resin. t-Box-L proline is bound to the resin, the t-Boc blocking group is removed, and the amino acid residues are introduced in the sequence identical to that described in Example 4.

EXAMPLE 7

L-(5-Oxoprolyl)-L-tyrosyl-L-arginyl-L-tryptophylglycyl-D-alanyl-L-leucyl-L-arginyl-L-prolyl amide The peptide resin of Example 5 is treated with hydrogen-fluoride-anisole to give the title peptide directly. Yield: 2.5 g. of crude product. A 1.25 g. sample of the crude product is purified in a manner similar to Example 3 to afford 327 mg. of the title peptide, shown to be homogeneous by thin-layer chromatography. Amino acid analysis: Glu, 0.99; Tyr, 1.00; Arg, 2.07; Trp, 0.98; Gly, 1.00; D-Ala, 0.99; Leu, 0.96; Pro, 1.05; and HN$_3$, 0.80.

EXAMPLE 8

L-(5-Oxoprolyl)-O-benzyl-L-tyrosyl-N$^g$-tosyl-L-arginyl-L-tryptophyl-L-prolin-polystyrene resin ester

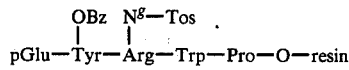

The title peptide resin is prepared and purified by the procedures described in Example 1 from 6 g. of t-Box-L-prolyl resin. The following amino acids are added to the t-Boc-L-prolyl resin in sequence: t-Boc-L-tryptophane, t-Boc-N$^g$-tosyl-L-arginine, t-Boc-O-benzy-L-tyrosine, and pyroglutamic acid.

EXAMPLE 9

L-(5-Oxoprolyl)-L-tyrosyl-L-arginyl-L-tryptophyl-N-ethyl-2-prolin amide

The peptide resin from Example 7 is treated with ethylamine according to the procedure described in Example 2 to cleave the blocked peptide from the resin. Yield: 1.69 g. Deblocking with hydrogen-fluoride-anisole according to the procedure described in Example 3 affords 3.1 g. of the crude title peptide. Gelfiltration on Sephadex G-10 in 2N acetic acid followed by partition chromatography with B-A-W (4:5:1), upper phase, affords 392 mg. of the title peptide, shown to be homogeneous by thin-layer chromatography.

EXAMPLE 10

The ability of the peptides of Formula I to inhibit spontaneous ovulation in warm-blooded animals is demonstrated by the following procedure:

Adult 180–200 g. female rats, maintained on a 14:10 light:dark lighting schedule and exhibiting two consecutive 4-day estrus cycles, receive subcutaneous injections of the test compound (in oil) on the afternoon of proestrus at 12:00, 12:30, 1:00, 1:30, 2:00, and 2:30. The rats are sacrificed the next morning (estrus), and the number of animals ovulating and the number of ova identified under a disecting microscope are recorded. The absence of, or a significant decrease in, the number of ova is the criterion for an anti-ovulary effect.

When tested in the manner above-described, the peptides of Examples 3, 5, 7, and 9, representative of the compounds of Formula I, gave the following results:

| Peptide | Dose (mg.) | Number of Ovulating Rats | % Inhibition of Ovulation |
|---|---|---|---|
| Example 3 | 6 | 0/5 | 100* |
| Example 5 | 6 | 2/5 | 60 |
| Example 7 | 0.5 | 3/6 | 50 |
| Example 9 | 6 | 2/4 | 50 |

*-CNS depression is noted at the anti-ovulatory dose

What is claimed is:
1. A peptide of the formula:

pGlu-Tyr-Arg-X-Y wherein:
X is Trp or D-Trp, and
Y is Pro—NHEt or the peptide segment —Gly—X$_1$—X$_2$—Arg—Pro—Z, wherein:
X$_1$ is Ala, D-Ala, or MeAla;
X$_2$ is Leu or D-Leu; and
Z is —NH$_2$ or —NHEt, or the non-toxic pharmaceutically acceptable acid addition salts thereof.

2. The peptide as defined in claim 1 which is L-(5—oxoprolyl)-L-tyrosyl-L-arginyl-D-tryptophylglycyl-(2-methylalanyl)—D-leucyl-L-arginyl-N-ethyl-L-prolinamide.

3. The peptide as defined in claim 1 which is 1-(5—oxoprolyl)-L-tyrosyl-L-arginyl-L-tryptophylglycyl-D-alanyl-L—leucyl-L-arginyl-N-ethyl-L-prolinamide.

4. The peptide as defined in claim 1 which is L-(5—oxoprolyl)-L-tyrosyl-L-arginyl-L-tryptophyl-glycyl-D-alanyl-L—leucyl-L-arginyl-L-prolyl amide.

5. The peptide as defined in claim 1 which is L-(5—oxoprolyl)-L-tyrosyl-L-arginyl-L-tryptophyl-N-ethyl-L-prolinamide.

* * * * *